United States Patent
Larsson

[11] Patent Number: 5,874,665
[45] Date of Patent: Feb. 23, 1999

[54] RHEOLOGICAL MEASURING DEVICE

[75] Inventor: Sven-Erik Larsson, Åkarp, Sweden

[73] Assignee: Reologica Instruments AB, Lund, Sweden

[21] Appl. No.: 858,740

[22] Filed: May 19, 1997

Related U.S. Application Data

[63] Continuation of PCT/SE95/01368, Nov. 17, 1995.

[30] Foreign Application Priority Data

Nov. 21, 1994 [SE] Sweden .................................. 9404014

[51] Int. Cl.$^6$ ..................................................... G01N 11/14
[52] U.S. Cl. .......................................... 73/54.28; 73/54.43
[58] Field of Search ................................ 73/54.28, 54.43, 73/54.32, 54.38

[56] References Cited

U.S. PATENT DOCUMENTS

| | | | |
|---|---|---|---|
| 2,266,733 | 12/1941 | Bays et al. | 265/11 |
| 3,111,838 | 11/1963 | Bucalo | 73/54 |
| 3,229,506 | 1/1966 | Bruss et al. | 73/59 |
| 3,292,423 | 12/1966 | Banks | 73/60 |
| 3,455,145 | 7/1969 | Gustafsson | 73/59 |
| 3,611,789 | 10/1971 | Lopas | 73/59 |
| 4,524,611 | 6/1985 | Richon et al. | 73/59 |
| 4,823,594 | 4/1989 | Gray | 73/54 |
| 5,042,292 | 8/1991 | Plint et al. | 73/60 |
| 5,209,108 | 5/1993 | Shackleford | 73/54.28 |
| 5,365,777 | 11/1994 | Layton | 73/54.28 |
| 5,540,088 | 7/1996 | Hall | 73/54.43 |

FOREIGN PATENT DOCUMENTS

| | | |
|---|---|---|
| 2 687 223 | 8/1993 | France . |
| 37 22 862 | 4/1988 | Germany . |
| 2 187 295 | 9/1987 | United Kingdom . |
| 2 275 342 | 8/1994 | United Kingdom . |
| WO 96/16324 | 5/1996 | WIPO . |

Primary Examiner—Hezron Williams
Assistant Examiner—J. David Wiggins
Attorney, Agent, or Firm—Merchant, Gould, Smith, Edell, Welter & Schmidt

[57] ABSTRACT

A rheological measuring device comprising a rotatable shaft 911), a first measuring body (12) operatively connected to a first end of said shaft (11) and a second measuring body (13) operatively connected to said first measuring body (12) through a sample medium (10). Said sample medium is enclosed in a sample chamber (14) defined by said second measuring body (13) and a slot seal (15) provided around said shaft (11) and being exposed to overpressure, said overpressure of the slot seal resulting in said sample medium being exposed to a pressure. Said pressure is transferred to said sample chamber through a space formed as a prechamber (19) formed in a lid (16) arranged over said second measuring body (13).

9 Claims, 1 Drawing Sheet

RHEOLOGICAL MEASURING DEVICE

This is a continuation of PCT/SE95/01368 application filed 17 Nov. 1995.

TECHNICAL FIELD

The invention relates to a rheological measuring device and in particular to a rheological measuring device for measuring under overpressure.

The viscosity or viscoelastic properties of a substance can be determined by means of a rheometer. The basic parts of a rheometer is a stand supporting a driving device and a measuring system (measuring bodies), or a measuring device which normally is mechanically connected to said driving device. Basically the measuring system corresponds to a sliding clutch, one side thereof being connected to the driving device of the rheometer and the other side thereof being fixedly mounted in said stand. The is sample constitutes the medium that transfers a torque from one side of the clutch to the second side of the clutch.

Frequently it is interesting to study how the Theological properties of the sample are affected by other physical quantities, such as temperature, pressure, illumination, electrical fields, etc., one by one or in combination.

BACKGROUND ART

The torques that will act as a load on doing the measuring of rheological zroerrties are normally very small, such as $10^{-7}$ to $10^{-2}$ Nm. The drive shaft of the rheometer is normally journalled in precision air bearings so as to provide such low torques. Other external torques of friction that will load the shaft therefore cannot be accepted. If there is a wish to perform the rheological measuring of the sample put under pressure the sample must be maintained under pressure, while at the same time a rotating movement is transferred to the sample. If the shaft is sealed with a box or other types of friction generating seals there will be a load from the frictional torque that is not desired.

It is previously known to enclose the sample in a closed measuring cell and to transfer a rotating movement without physical contact from a driving motor that constitutes the rheometer to the sample by means of magnets. In such an embodiment at least two major drawbacks will arise. Firstly, the closed measure cell will be classified as a pressure vessel for which specific safety regulations will apply. Secondly, the clutch or connection made of magnets will constitute an elastic connection which as a result of e.g. a slip will render dynamic measurings, e.g. such as oscillating movements of the driving motor, difficult or even impossible

DISCLOSURE OF THE INVENTION

An object of the present invention is to overcome the above stated problems existing in prior art and to accomplish a rheological measuring device providing a possibility of rheological measurements on a sample under pressure. Furthermore, the measuring device is arranged in such a way that basic components of conventional rheological measuring devices, such as e.g. the driving motor, the drive shaft and the measuring body connected to the drive shaft, can be used without any major modifications.

BRIEF DESCRIPTION OF THE DRAWINGS

The invention will now be described more in detail by means of practical embodiments, reference being made to the accompanying drawings, in which.

DETAILED DESCRIPTION

Figure 1:
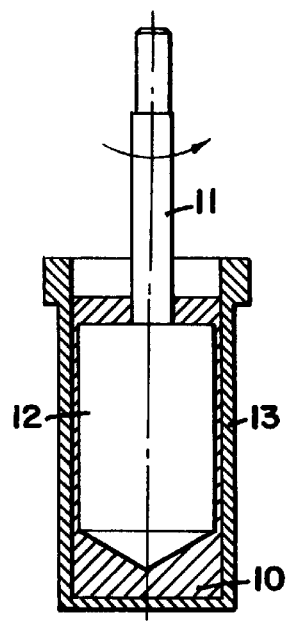
FIG. 1 is a sectional view schematically showing the basic principle of basic components of a conventional measuring device.

FIG. 1 shows schematically a conventional measuring arrangement of a concentric cylinder's type for rheological measurements. A drive shaft 11 is in a first end connected to a rheometer or a driving motor not shown in detail and in a second end connected to a bar-shaped first measuring body 12. Said first measuring body 12 is immersed into a second cylindric measuring body 13 open in one end. The sample or sample medium is inserted in said second measuring body 13, the sample constituting a connection between said first measuring body 12 and said second measuring body 13.

Basically, the rheological measurement can be carried out according to two different methods. According to a first method the rheometer motor shaft is rotated, and thereby also said drive shaft, according to prior art, e.g. by a constant number of revolutions per minute, and the transferred torque is measured. According to a second method the motor shaft receives a known torque, e.g. a constant torque, and the rotation of the shaft is measured.

Figure 2:
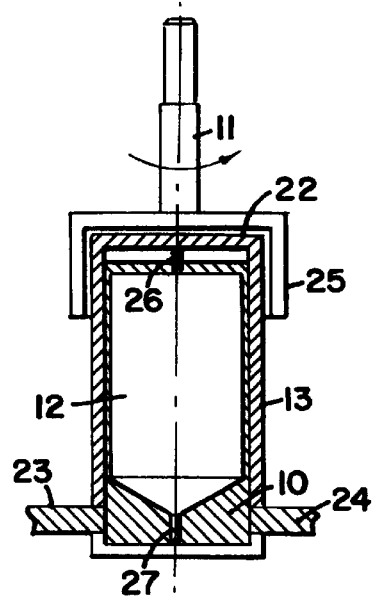
FIG. 2 is a sectional view schematically showing the principle of basic components of a prior art measuring device for measuring under pressure by means of a pressure cell.

The measuring device according to FIG. 1 cannot be used directly, if the viscoelastic properties of the sample are to be measured under pressure, i.e. the sample being exposed to a higher pressure than atmospheric pressure. However, FIG. 2 shows a measuring device available commercially for Theological measurements on samples that are exposed to pressure. Elements of the measuring device according to FIG. 2 having corresponding elements in the embodiment according to FIG. 1 have identical references.

The major difference between the embodiment according to FIG. 2 and the embodiment described above is that in the latter case the measuring system is a closed unit which is not mechanically connected to the rheometer or driving motor in a direct way. The second measuring body 13 is provided with a lid 22. Sometimes the measuring body 13 is formed as a completely closed cylinder. Said measuring body 13 is provided also with an inlet 23 and an outlet 24. The sample 10 is directed into and out of the cell through said inlet 23 and said outlet 24, respectively, through valves making it possible to expose the measuring cell to a higher pressure. For security reasons there is normally provided also a safety valve.

To transmit the rotating movement from the drive shaft 11 to the inner or first measuring body 12 the drive shaft 11 is provided with an external rotor 25 having magnetic poles, and said inner measuring body 12 is provided with permanent magnets. Said inner measuring body 12 is mounted in said outer or second measuring body 13 through bearing means 26, 27.

A major disadvantage with the embodiment according to FIG. 2 is that said inner and said outer measuring bodies are forced to take defined positions in relation to each other which will highly reduce the use of the measuring cell. A further disadvantage is that the rheometer according to FIG. 2 will drive two flexible couplings in serial, i.e. a magnetic coupling and a fluid clutch. Thereby the field of application will be substantially reduced. It will be more difficult to perform dynamic measurements under pressure and such measurements can be carried out only to a limited extent with a limiting lower frequency in the order of 1 Hz or lower.

Figure 3:
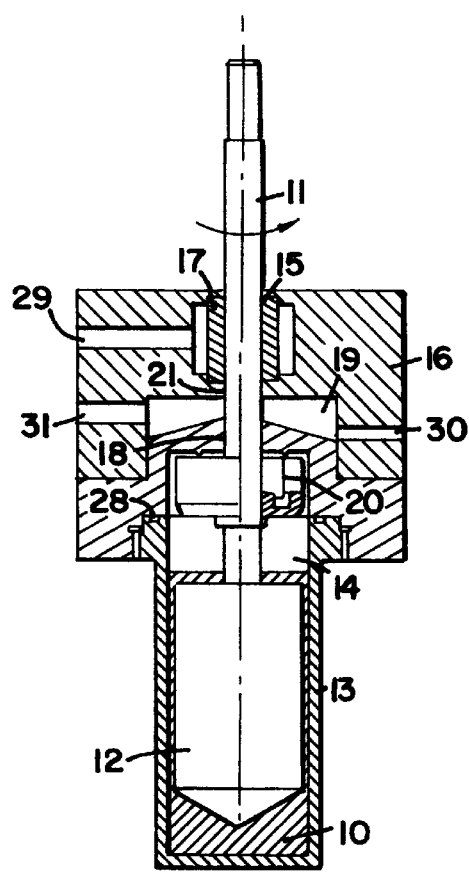
FIG. 3 is a view, partly a sectional view, schematically showing an embodiment of a measuring device according to the invention.

The embodiment according to FIG. 3 shows an example of a measuring device according to the invention. Similar to the embodiments according to FIG. 1 and FIG. 2 said measuring device comprises a drive shaft 11, a first inner measuring body 12, and a second outer measuring body 13. Said drive shaft 11 is mechanically connected to said inner measuring body 12.

The sample medium 10 is enclosed in a sample chamber 14 which is defined by said outer cylinder-shaped measuring body 13 and a lid 16 enclosing said measuring body having a slot seal 15 provided around said shaft 11 and being exposed to an overpressure. Said outer measuring body 13 is screwed into said lid 16 and sealed by an O-ring 28.

Said shaft 11 is surrounded by said slot seal 15 which in the embodiment shown comprises a porous bushing. The gap of the slot seal, or the difference between the outer diameter of the shaft 11 and the inner diameter of the bushing, is less than 0.1 mm.

The slot seal 15 is received in a first opening 17 in said lid 16. Said shaft 11 extends also through a second opening 18 which is displaced in relation to said slot seal 15 in the axial direction of said shaft 11 towards said measuring body 12. The difference between the outer diameter of said shaft 11 and the inner diameter of said second opening 18 is approximately 0.2 mm.

A space formed as a prechamber 19 is formed between said slot seal 15 and said second opening 18. Said prechamber 19 is put under pressure through said slot seal 15 and a third opening 21 formed between said prechamber 19 and said slot seal 15 in said lid 16. Between said sample chamber 14 and said prechamber 19 there is provided a liquid seal 20 enclosing said shaft 11.

The measuring cell is put under pressure in the following way. A gas, preferably air, is fed to said pushing or slot seal 15 under overpressure through a pressure inlet 29. The air will enter said prechamber 19 through said third opening 21. The pressure of the prechamber will be somewhat lower than the pressure in the pressure inlet 29. The difference in pressure between said prechamber 19 and the atmospheric pressure can be very large, and some air will also leak to the atmosphere through said slot seal. However, as the slot will provide a large resistance to air, the leakage will be comparatively small.

Said slot seal 15 or bushing will also to some extent act as a radial air bearing, i.e. stabilizing, centering and lubricating. Furthermore, some vibration of the shaft is allowed. The magnitude of the vibration can be larger than normally allowed of a shaft of a rheometer.

Said liquid seal 20 including in the embodiment shown a sleeve-shaped extension extending vertically from said lid is designed to prevent ventilation of the sample chamber. The pressure of the sample chamber is equal to the pressure of the prechamber. To prevent that sensitive samples will oxidize, an inert gas can be injected directly into the prechamber 19 under some overpressure. This can be done through a specially designed opening into said prechamber or through a draining opening 30 which is normally closed. Said inert gas can be inserted also through an opening 31 which is formed in said lid 16 to make it possible to measure the pressure in the prechamber and thereby also in the sample chamber.

According to the invention it is now possible to utilize such types of rheological measuring systems which normally are not used with a pressure cell also in connection with a pressure cell. No further frictional torques are added to the rotating system, that is the rheometer can be used all over its band width independently of the cell. The sample can be put into the measuring system the same way as without a cell, i.e. no inlet or outlet tubes for the sample medium or valves are needed. It is also possible to affect the sample conventionally in different ways, e.g. by heating or cooling the cell. The pressure of the cell is controlled externally and can easily be adjusted in any desired way, the pressure being independent of whether the sample of the cell is made to boil or not. The cell is not closed and the pressure within it cannot extend the pressure of the supplied gas.

The embodiment shown in FIG. 3 has been used as an example only and can be modified in many ways within the scope of the accompanying claims. The measuring bodies and the lid can be given quite different shapes from those shown in the Figure. Inlet and outlet openings can be formed in different parts and having different directions of flow than shown. There are no specific limits as to the material, said porous bushing may e.g. be formed by graphite or other materials having similar properties. It is also possible to provide said bushing as a tight sleeve having a number of small inlet holes disposed around the periphery of the sleeve, preferably symmetrically. the second opening 18 and the third opening are preferably made tapering in the longitudinal direction of said shaft 11 from said measuring body. In this way the insertion of the shaft into said lid 16 will be facilitated.

I claim:

1. Rheological measuring device, comprising a rotatable shaft, a first measuring body operatively connected to a first end of said shaft, and a second measuring body operatively connected to said first measuring body through a sample medium, wherein said sample medium is enclosed in a sample chamber which is defined by said second measuring body and a slot seal formed as a porous bushing surrounding said shaft, and said slot seal is connected to a pressure inlet for receiving a gas under overpressure and for supplying the sample chamber with gas and thereby exposing the sample chamber and said sample medium to an overpressure.

2. A rheological measuring device according to claim 1, wherein:

a lid is provided over said second measuring body, said slot seal is received in a first opening of said lid, said shaft extends through said slot seal and through a second opening in said lid displaced in relation to said slot seal in the axial direction of said shaft towards said first measuring body.

3. A rheological measuring device according to claim 2, wherein:

a space formed as a prechamber is formed between said slot seal and said second opening.

4. A rheological measuring device according to claim 3, wherein:

a liquid seal surrounding said shaft is provided between said sample chamber and said prechamber.

5. A rheological measuring device according to claim 1, wherein:

said porous bushing is made from graphite.

6. A rheological measuring device according to claim 2, wherein:

said second opening in said lid is tapered in the longitudinal direction of said shaft from said first measuring body.

7. A rheological measuring device according to claim 3, wherein:

a third opening connecting said prechamber and said first opening and receiving said shaft is made tapering in the longitudinal direction of said shaft from said first measuring body.

8. A rheological measuring device according to claim 3, wherein:

said prechamber is operatively connected to a pressure measuring means.

9. A rheological measuring device according to claim 1, wherein:

said slot seal is formed as a sleeve having a plurality of small inlet holes disposed around the periphery of said sleeve.

* * * * *